United States Patent [19]
Endo et al.

[11] Patent Number: 4,697,581
[45] Date of Patent: Oct. 6, 1987

[54] ELECTROMAGNETIC VIBRATION GENERATOR

[75] Inventors: Yoichi Endo, Tokyo; Kazumi Masaki, Osaka, both of Japan

[73] Assignee: Ken Hayashibara, Okayama, Japan

[21] Appl. No.: 718,431

[22] Filed: Apr. 1, 1985

[30] Foreign Application Priority Data

| Apr. 4, 1984 | [JP] | Japan | 59-67013 |
| Apr. 10, 1984 | [JP] | Japan | 59-69929 |
| Aug. 15, 1984 | [JP] | Japan | 59-170207 |

[51] Int. Cl.⁴ ............................................. A61H 23/02
[52] U.S. Cl. ...................................... 128/41; 128/33; 128/424; 310/29
[58] Field of Search ................. 128/33, 41, 424; 310/29

[56] References Cited

U.S. PATENT DOCUMENTS

| 1,498,679 | 6/1924 | Clement | 128/41 |
| 1,945,675 | 2/1934 | Binney | 128/41 |
| 2,135,312 | 11/1938 | Muckle | 128/41 |
| 2,227,276 | 12/1940 | Salit | 128/41 |
| 2,582,617 | 1/1952 | August | 128/41 |
| 2,840,071 | 6/1958 | McNair | 128/41 |
| 2,943,621 | 7/1960 | Phillips | 128/41 |
| 4,064,376 | 12/1977 | Yamada | 128/33 |
| 4,326,506 | 4/1982 | Kawabata | 128/33 |
| 4,354,067 | 10/1982 | Yamada et al. | 128/33 |
| 4,465,158 | 8/1984 | Yamazaki | 128/33 |

FOREIGN PATENT DOCUMENTS

| 2745002 | 7/1978 | Fed. Rep. of Germany | 128/33 |
| 1304736 | 4/1962 | France | 128/33 |
| 416248 | 9/1934 | United Kingdom . | |
| 713113 | 8/1954 | United Kingdom . | |
| 893868 | 4/1962 | United Kingdom . | |
| 993486 | 5/1965 | United Kingdom | 128/41 |
| 1392383 | 4/1975 | United Kingdom . | |
| 1579889 | 11/1980 | United Kingdom . | |
| 1585726 | 3/1981 | United Kingdom . | |

Primary Examiner—Clyde I. Coughenour
Attorney, Agent, or Firm—Browdy and Neimark

[57] ABSTRACT

A novel electromagnetic vibration generator, wherein a coil member capable of generating magnetic line of force and its magnetic counterpart are placed in parallel and united in one body in such a manner that the coil member and magnetic counterpart form a uniform gap, is disclosed. A coil member and a vibration plate are feasible as the magnetic counterpart. The vibration generator is driven by supplying an alternating current to the coil member so that a set of coil member successively attract or repel each other, or that the magnetomotive force of single coil member successively attracts the vibration plate. The vibration generator is vibrotherapeutically effective in the vibration frequency range of 50-80 times/sec, and 100-280 times/sec.

10 Claims, 20 Drawing Figures

ELECTROMAGNETIC VIBRATION GENERATOR

FIELD OF THE INVENTION

The present invention relates to a vibration generator, more particularly, it relates to an electromagnetic vibration generator feasible in a vibrotherapeutic apparatus directed to induce and/or accelerate hypnosis and vigilance, as well as to treat the stiffness of the shoulder, myalgia, lumbago, arthritis, rheumatism, feeling of cold, etc.

BACKGROUND OF THE INVENTION

Although a vibration generator system for massaging apparatus wherein the vibration is generated by a successive attack on a vibration plate with an eccentric weight, equipped at the rotary shaft of an electromotor, is known, this system has some demerits that its whole structure is unduly large in size, as well as that the vibration plate and eccentric weight unceasingly generate noisy attacks during its use. These restrict its practical use.

BRIEF DESCRIPTION OF THE DRAWINGS

Throughout the Figures, (1) means coil member capable of generating the magnetic line of force; (2), supporting member; (3), magnetic core; (4), buffering member; (5), vibration generator according to the invention; (6), blanket; (7), cushion; (8), vibration plate; (9), cover; (10), elastic plate; (11), plate member; (12), edge of plate member (11), (13), catch; (14), pliable supporting member; AC, ac power source; T, time switch or time-switched current regulating circuit; D, diode; SCR, thyristor; A, rectifier; C, capacitance; O, oscillator; S, switch; and G, phase-regulating circuit.

DESCRIPTION OF THE PREFERRED EMBODIMENTS

The present invention provides a vibration generator system which is freely placeable in beddings, e.g. blanket and "FUTON" (a thick bedquilt), and clothing, e.g. vest, cap, hat, "TABI" (digitated socks) and "TANZEN" (a padded large-size "KIMONO"), wherein the above-mentioned demerits of the conventional vibration generator system are overcome.

More particularly, the present invention relates to the electromagnetic vibration generator having a novel structure, comprising a coil member capable of generating a magnetic line of force; and its magnetic counterpart, wherein the coil member and its magnetic counterpart are placed in parallel and united in one body in such a manner that they form a uniform gap.

The present invention will be more clearly understood with reference to the Figures.

FIGS. 2–11 illustrate the vibration generator according to the invention.

FIGS. 2–5 show some embodiments wherein a set of coil members (1) and (1) are placed in parallel and united in one so that the coil members form a uniform gap.

Figure 1:
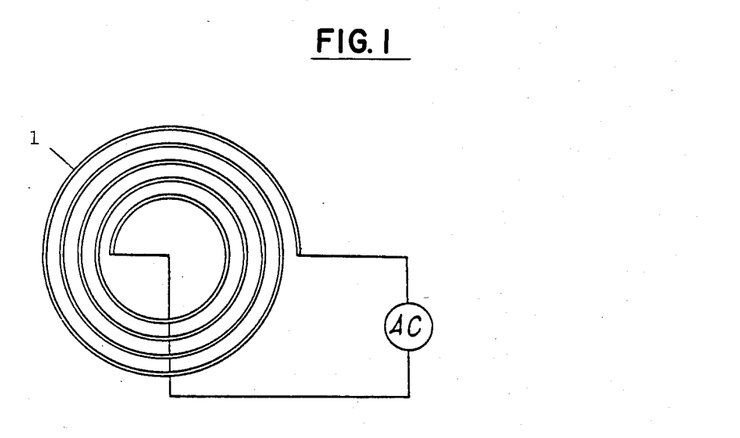
FIG. 1 shows the plan view of coil member capable of generating the magnetic line of force.
Figure 2:
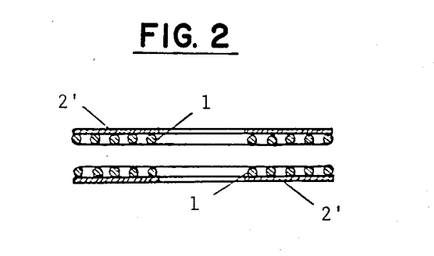
FIGS. 2–5 show the vertical sectional views of some embodiments according to the invention.
Figure 3:
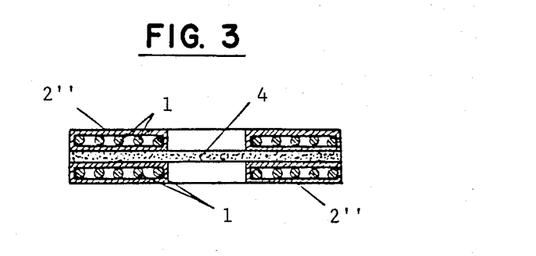
Figure 4:
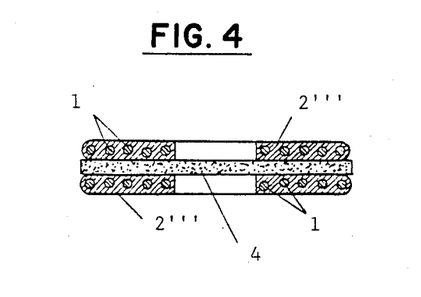
Figure 5:
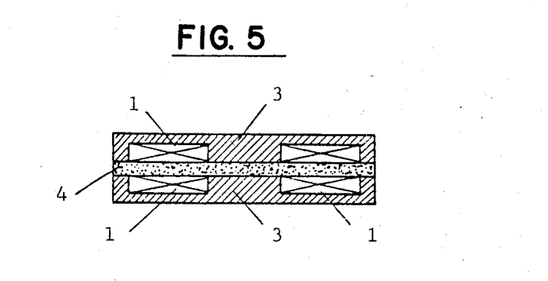
Figure 6:
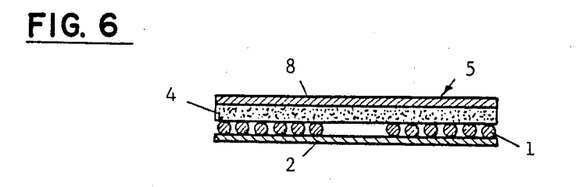
FIGS. 6–9 show the vertical sections of some embodiments according to the invention.

In FIGS. 2–4, coil member (1) is flatly formed, e.g. spirally, particularly as shown in FIG. 1. Coil member (1) is supported in one body by supporting member (2), e.g. either supporting plate (2)' as shown in FIG. 2, case (2)" as shown in FIG. 3, or cover (2)''' as shown in FIG. 4, in order that a uniform vibration is generated on the whole, as well as that coil member (1) can be easily handled. Although cloth, rubber, synthetic resin and metal are employable as the material for supporting member (2), the use of a pliable material is desirable. As shown in FIG. 5, coil member (1) having magnetic core (3), e.g. compressed iron powder, may be used in order to strengthen the magnetic line of force. A set of coil members (1) and (1) are placed in parallel as shown in FIG. 2 to form a uniform gap of an appropriate distance. As shown in FIGS. 3–5, the interposition of pliable buffering member (4), such as sponge, rubber, cloth or paper, between the coil members is effective, as well as in keeping such distance, in smoothly vibrating coil members (1) and (1). When coil members (1) and (1) are supplied with an alternating current from an ac source, the coil members generate the magnetic line of force, and attract or repel each other dependent on the directions of the magnetic line of force to generate a vibration. Each coil member (1) may be supplied with the alternating current from the same or different power source(s), in relation to the connection of the coil members.

FIGS. 6–9 show some embodiments wherein coil member (1) and vibration plate (8) are placed in parallel, and united in one body so that they form a uniform gap.

Figure 7:
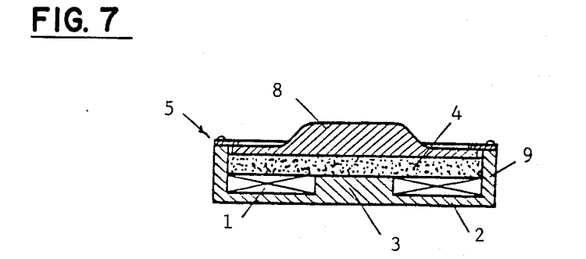
Figure 8:
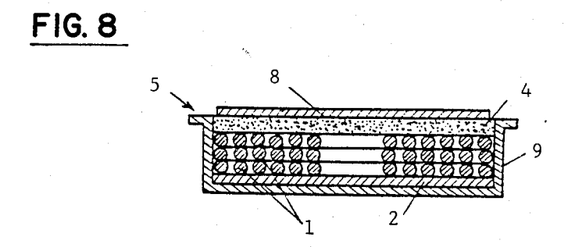
Figure 9:
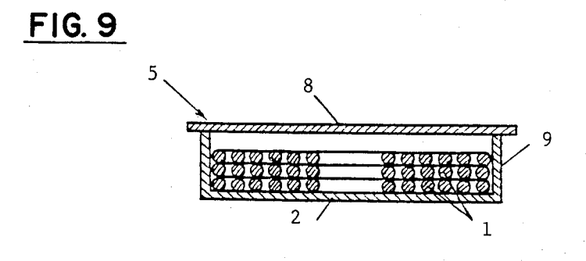

Coil member (1) is flatly formed, e.g. spirally, particularly as shown in FIG. 1. The use of coil member (1) having magnetic core (3), e.g. compressed iron powder, as shown in FIG. 7 is effective to strengthen the magnetic line of force. Supporting member (2) is composed of rubber, synthetic resin, metal, etc., and closely fixes one side of coil member (1). The use of supporting member (2) of a ferromagnetic metal is desirable to strengthen the magnetic line of force similarly as in coil member (1). Magnetic core (3) may be united in one body with supporting member (2). Vibration plate (8) is also composed of a material having a high magnetic permeability, e.g. ferromagnetic metal such as iron, nickel, cobalt, alloys thereof and ferrites, so that it is attracted or repelled by the magnetic line of force. The center of the vibration plate may be swollen as shown in FIG. 7. Vibration plate (8) is placed over one side of coil member (1) so that they form a uniform gap with an appropriate distance. Although the distance can be kept with a spring member, the interposition of pliable buffering member (4), e.g. sponge, rubber, cloth, paper, etc., is much more effective, as well as in keeping such distance, in smoothly driving vibration plate (8). Cover (9) shields coil member (1), and may be united with supporting member (2) to form a container structure. Cover (9) may be composed of synthetic resin or metal. The merits of using a ferromagnetic metal for cover (9) include that the resistance in the magnetic circuit is reduced, that pliable buffering member (4) is effectively protected, and that vibration generator (5) can be united in one body. Vibration plate (8) is driven by supplying an alternating current from an ac power source to coil member (1) associated with vibration plate (8). Coil member (1) generates a magnetomotive force and attracts vibration plate (8) when non-zero current is charged, while vibration plate (8) returns to the former position when the magnetomotive force disappears. Thus, the vibration is generated.

Figure 10:
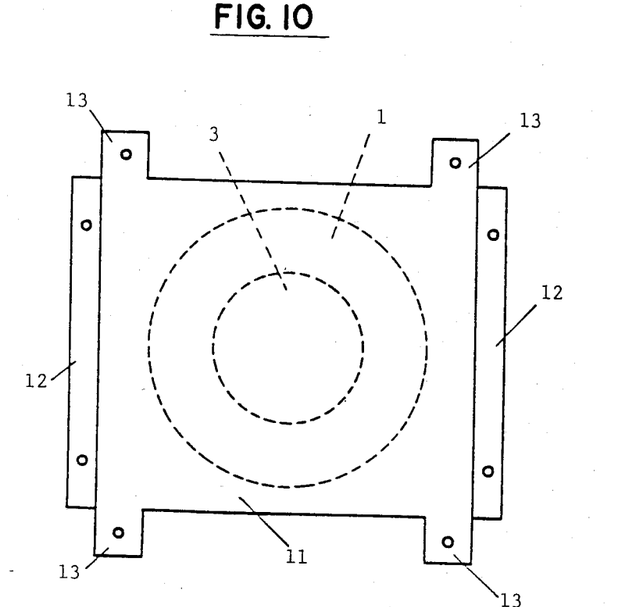
FIGS. 10 and 11 respectively show the plan- and side elevation-views of an embodiment.
Figure 11:
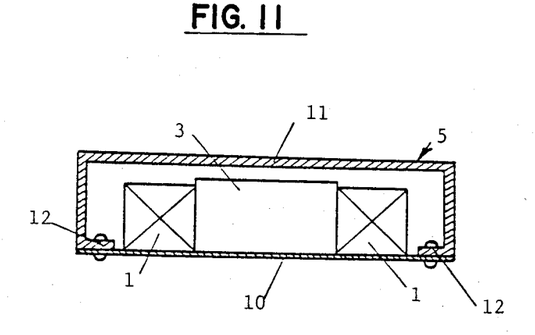

FIG. 10 and 11 show an embodiment wherein coil member (1) is fixed on the inside wall of elastic plate (10), and wherein the elastic plate and plate member (11) with a high magnetic permeability are placed in parallel and united in one body. Elastic plate (10) may be composed of, e.g. rubber, synthetic resin, metal, etc., but equipped with coil member (1) having magnetic core (3). Plate member (11) is made of a ferromagnetic metal, e.g. iron, nickel, etc., or composed by laminating a ferromagnetic metal on an elastic plate. Plate member (11) forms a U-shaped frame, and a set of opposite edges (12) and (12) are L-shaped inwardly or outwardly. Elastic plate (10) is supported over plate member (11) by screwing or riveting at the edges. Elastic plate (10) is placed over coil member (1) having magnetic core (3) in so that elastic plate (10) and plate member (11) form a uniform gap of an appropriate distance. Elongated parts of plate member (11) is shaped into catch (13) which is used to equip the vibration generator on pliable supporting member (14), e.g. mattress, etc. Coil member (1) generates a magnetomotive force, and magnetic core (3) attracts plate member (11) when non-zero current is charged, while plate member (11) returns to the former position when the current is suspended and the magnetomotive force disappears. When coil member (1) is supplied with an alternating current, the coil member generates a successive magnetomotive force at a prescribed period, and the vibration generator composed of plate member (11), coil member (1) containing magnetic core (3), and elastic plate (10), therefore, attracts and returns at the same period to generate a vibration. The vibration is generally transmitted through plate member (11), and used. A weight ratio of coil member (1) containing magnetic core (3) to plate member (11) in the range of 1 to several folds, particularly, 1/3-3-folds, is preferred with the viewpoint of an effective transmission of vibration energy.

Figure 12:
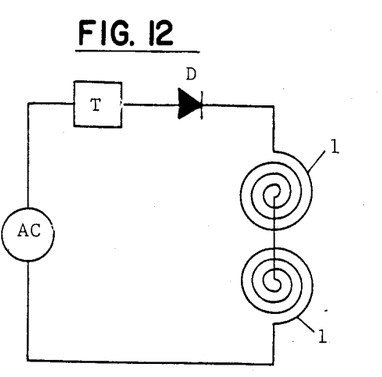
FIG. 12 shows the wiring diagram of an embodiment wherein a diode is used.

The electric circuit shown in FIG. 12 illustrates an embodiment wherein a current from ac power source AC is supplied to diode D through time-switched current regulating circuit T to obtain a successive half sine wave feasible for driving coil members (1) and (1).

Figure 13:
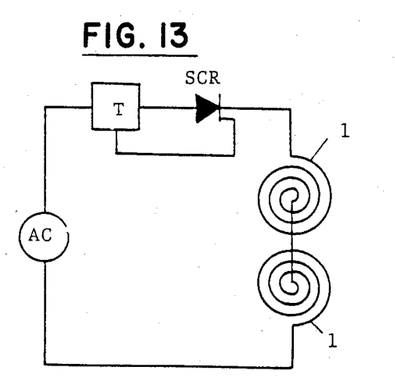
FIG. 13 shows the wiring diagram of an embodiment wherein a thyristor is used.

The electric circuit shown in FIG. 13 illustrates another embodiment wherein a current from ac power source AC through time-switched current regulating circuit T is successively discharged through thyristor SCR to obtain an alternating current feasible for driving coil members (1) and (1).

Figure 14:
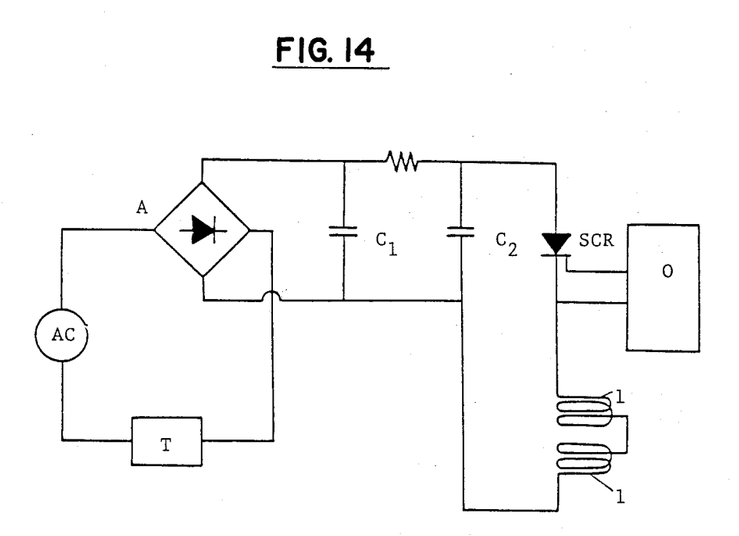
FIG. 14 shows the wiring diagram of an embodiment wherein the vibration frequency is variable.

The electric circuit shown in FIG. 14 illustrates still another embodiment wherein coil members (1) and (1) are driven with an alternating current different in frequency from the source current to be used. The current from ac power source AC is rectified, and smoothed by rectifier A and capacitance $C_1$, after which the smoothed current is charged in capacitance $C_2$, and successively discharged through thyristor SCR to obtain such alternating current. The alternating current is supplied to coil members (1) and (1) to vibrate them. The frequency of the alternating current can be set to a suitable level by controlling the oscillation frequency of oscillator O.

The electric circuits as shown in FIGS. 12–14 are also suitable for driving the vibration generators as shown in FIGS. 6–11.

Figure 15:
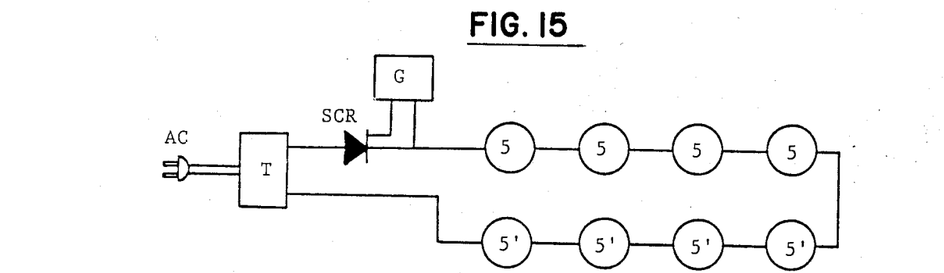
FIGS. 15 and 16 show the electric circuits which are feasible for supplying electricity to the vibration generator according to the invention.
Figure 16:
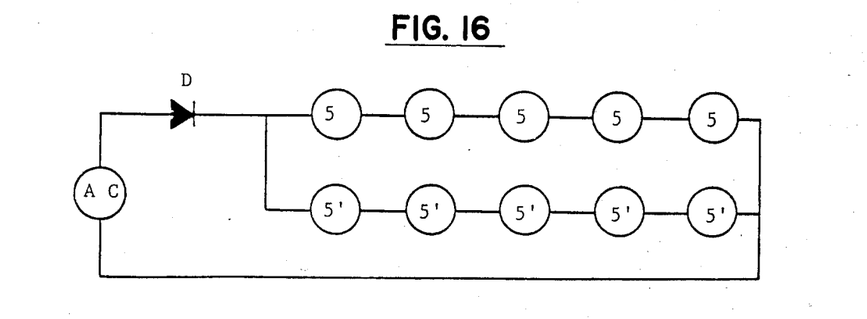
Figure 17:
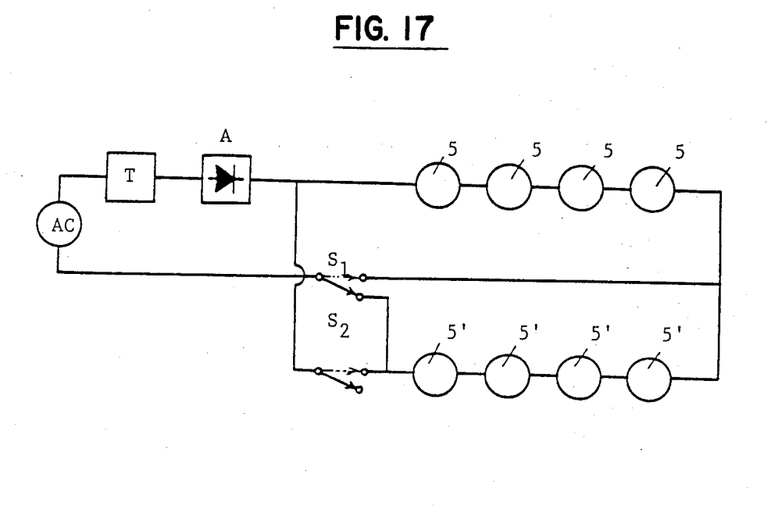
FIG. 17 shows the wiring diagram of an embodiment wherein the connection of plural vibration generators is switcheable.

FIGS. 15–17 illustrate some manners of supplying electricity to the vibration generator according to the invention.

In the manner as shown in FIG. 15, an power source AC is connected to vibration generators (5), (5), . . . , (5)', (5)', . . . through time switch T and thyristor SCR. Thyristor SCR is power-regulated by, e.g. phase-regulating circuit G, and supplies an alternating current of a prescribed magnitude to vibration generators (5), (5), . . . , (5)', (5)', . . . at prescribed intervals.

In FIG. 16, sine wave from ac power source AC is rectified by diode D, and the resultant successive half sine wave is supplied to two groups of vibration generators (5), (5), . . . , and (5)', (5)', . . . connected in parallel.

In FIG. 17, an ac current is supplied to two groups of vibrators (5), (5), . . . , and of (5)', (5)', . . . from ac power source AC through time switch T and rectifier A. By switching switches $S_1$ and $S_2$ as shown with the solid lines, a group of vibrators (5), (5), . . . and the other group of vibrators (5)', (5)', . . . are connected in series, while two groups of the vibrators are connected in parallel when these switches are switched as shown with the chain lines. The parallel connection is preferable when a relatively large vibration amplitude of vibration plate (8) is desired, and the series connection is employed to obtain a relatively small vibration amplitude.

Figure 18:
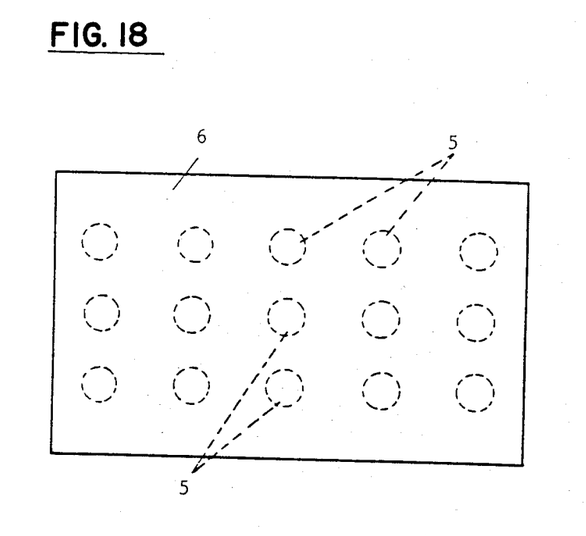
FIG. 18 shows the plan view of an application wherein plural vibration generators are placed within a blanket.

FIG. 18 shows an application wherein plural vibration generators (5), (5), . . . according to the invention are placed within blanket (6).

Figure 19:
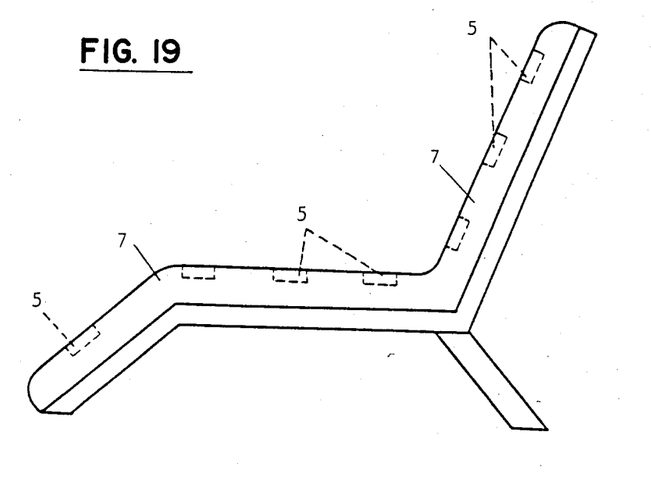
FIG. 19 shows the side elevation view of another application wherein plural vibration generators are embedded within the cushions of an upholstered chair.

FIG. 19 shows another application wherein plural vibration generator (5), (5), . . . according to the invention are embedded within cushions (7) and (7) of an upholstered chair.

Figure 20:
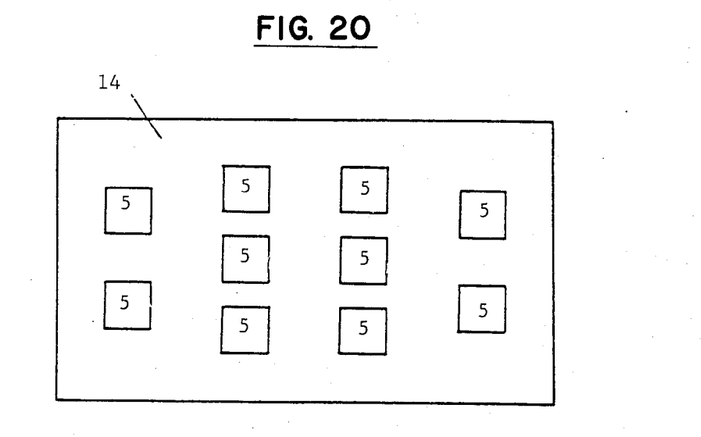
FIG. 20 shows the plan view of an embodiment wherein plural vibration generators are equipped within a pliable supporting member.

The vibration generator according to the invention may be embedded within pliable supporting member (14) having appropriate dimensions, e.g. sponge, rubber, etc. As shown in FIG. 20, two or more vibration generators (5), (5), . . . are generally equipped within pliable supporting member (14), such as mattress.

As described above, since the vibration generator according to the present invention substantially consists of the coil member and its magnetic counterpart, the vibration generator is not large on the whole, and freely placeable in or on beddings, such as blanket, "FUTON" and bed; clothing, such as vest, cap, hat, "TABI" and "TANZEN"; and furniture, such as chair, to locally or systemically expose a human body to an effective dose of the magnetic line of force in order to take a kink out of the muscle by expansion and contraction and also to facilitate the blood circulation. We found that our vibration generator is effective in the induction and/or acceleration of hypnosis and vigilance, as well as in the treatment of the stiffness of the shoulder, myalgia, lumbago, arthritis, rheumatism, feeling of cold, etc.

According to the results of our experiments, the vibration frequency in the ranges of 50-80 times/sec, 100-120 times/sec, and of over 120 up to 280 times/sec are most stimulative to the muscles. It was confirmed that a remarkable vibrotherapeutic effect can be obtained with a vibration frequency in these ranges. A sound wave, simultaneously generated and having the above vibration frequency, is also therapeutically effective. We found that a vibration and a sound wave having a vibration frequency over 120 times/sec, particularly over 120 up to 280 times/sec, exhibit a remarkable antihypnotic effect. By associating a time switch with an apparatus for switching the vibration frequency, hypnosis of a person is accelerated for a prescribed time, after which vigilance is forced. Embedding of the vibration generator(s) within the headrest or seat in a motor-car effectively prevents the dozing off of the driver.

While the described embodiments represent the preferred forms of the present invention, it is to be understood that modifications will occur to those skilled in the art without departing from the spirit of the invention. The scope of the invention is therefore to be determined solely by the appended claims.

We claim:

1. An electromagnetic vibration generator comprising
    an elastic plate member;
    a solenoid having a magnetic core attached on said elastic plate member;
    a rigid casing member mounted over said plate member and made of a magnetic conductive material;
    said rigid casing member being supported at least on a pair of opposite edges over said elastic plate member with a surface of said solenoid opposite from a surface facing said elastic plate member uniformly distanced from a wall of said rigid casing member facing said solenoid to form a gap to cause a perpendicular vibratory motion of a frequency in the range of 50 to 80 times a second or 100 to 280 times a second when energized with an alternating current of the same frequency in either range;
    the weight ratio of said solenoid to said rigid casing member being substantially 1 to 9.
2. The electromagnetic vibration generator of claim 1 wherein
    said solenoid has a coil member in flat form.
3. The electromagnetic vibration generator of claim 1 wherein
    said solenoid has a coil member in spiral form.
4. The electromagnetic vibration generator of claim 1 further including
    another coil member capable of generating magnetic lines of force.
5. The electromagnetic vibration generator of claim 1 wherein
    said magnetic core is made of a ferromagnetic metal.
6. The electromagnetic vibration generator of claim 1 wherein
    said magnetic core is made of a member selected from a group consisting of iron, nickel, cobalt, alloys thereof, and ferrites.
7. The electromagnetic vibration generator of claim 1 wherein
    a buffering member is placed within said gap.
8. The electromagnetic vibration generator of claim 1 wherein
    said buffering member is made from a material selected from a group consisting of sponge, rubber, cloth, and paper.
9. The electromagnetic vibration generator of claim 1 wherein
    said solenoid member has a coil member;
    said elastic plate member has a high elasticity;
    said casing member has a high magnetic permeability as the magnetic counterpart of said coil member;
    said coil member is fixed on said elastic plate member; and
    said casing member is placed over said coil member and united in one body to form a uniform gap.
10. The electromagnetic vibration generator of claim 9 wherein
    said elastic plate member is made from a material selected from a group consisting of rubber, synthetic resin and metal.

* * * * *